United States Patent [19]
Smith

[11] Patent Number: 5,562,654
[45] Date of Patent: Oct. 8, 1996

[54] TIME-RELEASED DELIVERY SYSTEM

[75] Inventor: Todd T. Smith, Lexington, Ky.

[73] Assignee: University of Kentucky Research Foundation, Lexington, Ky.

[21] Appl. No.: 330,896

[22] Filed: Oct. 28, 1994

[51] Int. Cl.$^6$ .................................................. A61K 9/22
[52] U.S. Cl. .................. 604/892.1; 604/96; 604/104; 606/193
[58] Field of Search .............................. 604/890.1, 891.1, 604/892.1, 96–99, 104; 606/193

[56] References Cited

U.S. PATENT DOCUMENTS

| | | |
|---|---|---|
| 3,256,884 | 6/1966 | Hill et al. . |
| 3,995,631 | 12/1976 | Higuchi ................................ 604/892.1 |
| 4,100,923 | 7/1978 | Southern ................................ 604/96 |
| 4,119,098 | 10/1978 | Bolduc et al. ............................ 604/96 |
| 4,340,054 | 7/1982 | Michaels . |
| 4,455,144 | 6/1984 | Michaels . |
| 4,578,076 | 3/1986 | Luukkainen et al. ..................... 604/892 |
| 4,816,020 | 3/1989 | Brownell et al. ......................... 604/97 |
| 5,030,216 | 7/1991 | Theeuwes et al. . |
| 5,084,004 | 1/1992 | Ranoux . |
| 5,372,584 | 12/1994 | Zink et al. ............................... 606/193 |

FOREIGN PATENT DOCUMENTS 3713404  11/1988  Germany ........................... 604/892.1

*Primary Examiner*—Randall L. Green
*Assistant Examiner*—Chalin Smith
*Attorney, Agent, or Firm*—King and Schickli

[57] ABSTRACT

An apparatus is provided for the time-released delivery of a selected preparation into a patient's uterine cavity. The apparatus includes an osmotic pump for expelling the selected preparation over time and a catheter for delivery the expelled preparation into the uterine cavity. An inflatable balloon on the catheter holds the apparatus in position in the patient.

14 Claims, 1 Drawing Sheet

U.S. Patent   Oct. 8, 1996   5,562,654

TIME-RELEASED DELIVERY SYSTEM

TECHNICAL FIELD

The present invention relates generally to the medical field, and more particularly to an apparatus and method for the reliable, time-released delivery of a selected preparation, such as medicinal preparations for the treatment of infection or sperm cell suspensions for purposes of artificial insemination, into a patient's uterine cavity.

BACKGROUND OF THE INVENTION

It has been estimated that 15% of couples in the United States are unable to conceive within one year of the first attempt at conception and nearly 3 million of such couples seek medical help annually. Further studies have shown that infertility may be contributed to the male 35% of the time and the female 55% of the time with the remaining 10% being undetermined.

Economic pressures, the women's liberation movement and other social factors caused many women in the 1970's and 1980's to forego child bearing and raising of a family in favor of pursuit of a career. Now many of those women are interested in starting a family, but the postponement of pregnancy has resulted in significantly increased rates of infertility. Further, increasing incidences of pelvic inflammatory diseases are also thought to be a major reason for increases in infertility. Specifically, such pelvic infections lead to the formation of scar tissue around the ovaries and the fallopian tubes which impedes the transport of oocytes for fertilization. Additionally, ovulatory dysfunction accounts for a substantial percentage of infertility cases.

From the above, it should be appreciated that the treatment of infertility is an important medical science issue and at present, it is a growing concern.

It may also be estimated that over 1 million artificial insemination procedures have been performed in the United States during each of the last three years. Generally, intrauterine insemination is broadly utilized in the treatment of infertile couples including, for example, those wherein the female is suffering from mucus hostility or the male suffers from moderately abnormal semen parameters. The most commonly utilized intrauterine insemination technique is the bolus technique which comprises the single deposition of a very large number of spermatozoa into the uterine cavity. For example, a deposition of 0.6 ml of spermatozoa preparation may be injected into the uterus of the patient.

This sudden and relatively high concentration of spermatozoa in the uterine cavity contrasts sharply with the relatively slow release of small numbers of spermatozoa from the endocervix into the upper genital tract following natural intercourse. It has therefore, been suggested that the bolus technique may not be particularly effective in achieving conception since the produced effect contrasts sharply with the slow and gradual stages of sperm transport into the fallopian tube resulting from natural intercourse.

Toward this end, Nabil S. Mubarib and his associates have previously developed a slow release intrauterine insemination technique relying on an auto-syringe driver providing for the delivery of approximately $50 \times 10^3$ spermatozoa every minute for three hours. While this slow release intrauterine insemination technique has shown some promise, it does suffer from several shortcomings. First, the patient must remain in a supine position for the full three hour treatment period. Thus, the treatment procedure is time consuming and inconvenient. Second, the slow delivery of spermatozoa for even a three hour period is still not of sufficient duration to accurately mimic the prolonged slow release of small numbers of spermatozoa that occurs naturally over a period of up to 24 hours or more. Thus, a need is identified for an improved method for slow release intrauterine insemination.

Further, it should also be appreciated that many infectious diseases including but not limited to endometritis, pelvic inflammatory disease, endomyometritis and cervicitis may best be treated with the prolonged time-released delivery of a selected preparation of antibiotics such as penicillins, erythromycins, cephalosporins and metronidazole. Thus, a further need is identified for a more versatile apparatus for allowing the time-released delivery of a selected preparation into a patients uterine cavity where that selected preparation may, for example, be a spermatozoa preparation for artificial insemination or a medical preparation of drugs/antibiotics for treatment of diseases such as inflammatory infections.

SUMMARY OF THE INVENTION

Accordingly, it is a primary object of the present invention to provide a versatile apparatus and method for the time-released delivery of a selected preparation into a patient's uterine cavity. That selected preparation may be a spermatozoa preparation/sperm cell suspension for slow release intrauterine insemination as a treatment for infertility, an antibiotic preparation for the treatment of various female reproductive system inflammations, infections and diseases, or other medicinal preparation that may be appropriately delivered or administered to the patient in the manner described.

Yet another object of the present invention is to provide an improved apparatus for the time-released delivery of a selected preparation into a patient's uterine cavity that allows for the slow, time-released delivery of a selected preparation over a long or extended period of time of up to 24 hours or more. Advantageously, the apparatus includes a retaining mechanism to hold the apparatus in position during the treatment period while otherwise allowing the patient to proceed with unimpeded normal physical activities.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved apparatus is provided for the time-released delivery of a selected preparation into a patient's uterine cavity. The apparatus includes an osmotic pump for expelling the selected preparation over time. The osmotic pump is connected to a catheter. The catheter has a proximal end in fluid communication with the osmotic pump for receiving the selected preparation expelled by the osmotic pump and a distal end for delivery of the expelled preparation into the uterine cavity of the patient. Further, the apparatus includes a means, in the form of an inflatable balloon, for retaining the apparatus in position in the patient. Specifically, the osmotic pump is preferably held in the patient's vagina and the distal end of the catheter is held in the patient's uterine cavity.

More specifically, the osmotic pump is of a type known in the art. The pump is constructed to be of small size so as to fit comfortably into the vagina. The pump includes an inner reservoir chamber for holding a charge or predetermined amount of the selected preparation. The osmotic pump also includes an outer chamber for holding an osmotically active agent. An impermeable membrane separates the inner and outer chambers and a semi-permeable membrane separates the outer chamber from the external environment.

During the treatment period, water from vaginal secretions crosses the semi-permeable membrane and enters the outer chamber. As more and more water enters the outer chamber, the osmotically active agent swells and greater and greater pressure is applied upon the inner reservoir chamber. Accordingly, the inner reservoir chamber is slowly compressed and the resulting reduction in volume causes the selected preparation to be slowly expelled through the catheter into the uterine cavity. More specifically describing the apparatus of the invention, the catheter is a double lumen catheter. It is the first lumen of this catheter that has a proximal end connected in fluid communication with the osmotic pump and a distal end for delivering the expelled selected preparation into the uterine cavity of the patient.

The inflatable balloon for retaining the apparatus in position is in fluid communication with a first end of the second lumen which is received in the uterine cavity of the patient. The opposite or second end of the second lumen is connected to a coupling. This coupling includes a check valve of a type known in the art and is also adapted to receive a syringe. The syringe is used to deliver air into the inflatable balloon.

In accordance with yet another aspect of the present invention a method of providing for the time-released delivery of a selected preparation into the patient's uterine cavity is provided. The method includes the initial step of charging the osmotic pump with the selected preparation. Next is the positioning of the apparatus in the patient so that the osmotic pump is held in the patient's vagina and the catheter extends through the patient's cervical canal into the patient's uterine cavity. This is then followed by the step of positively retaining the apparatus in position.

As should be appreciated from above, this is done by providing the inflatable balloon on the end of the catheter that is inserted into the uterine cavity. More specifically, the catheter is inserted into the uterine cavity so that the balloon is just above the endocervix. The balloon is then inflated utilizing the syringe. The syringe is then removed and the check valve prevents air from escaping from the balloon. With the apparatus retained in position in this matter, the patient may then advantageously proceed with various physical activities and most patients may actually complete their normal daily routine. The apparatus is retained in place by the inflatable balloon throughout the treatment period of up to 24 hours or more during which time a slow and gradual time release of the preparation continuously occurs. As described above, such gradual and continuous administration of a sperm cell suspension enhances the treatment of infertility and is more likely to lead to conception. Further, such gradual and continuous administration of an antibiotic is more likely to lead to the successful treatment of various infectious diseases of the reproductive tract. Of course, it should also be appreciated that the device may not only be utilized to treat humans but also to treat various mammals and, particularly, domestic farm animals.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing.

Figures 1, 2:
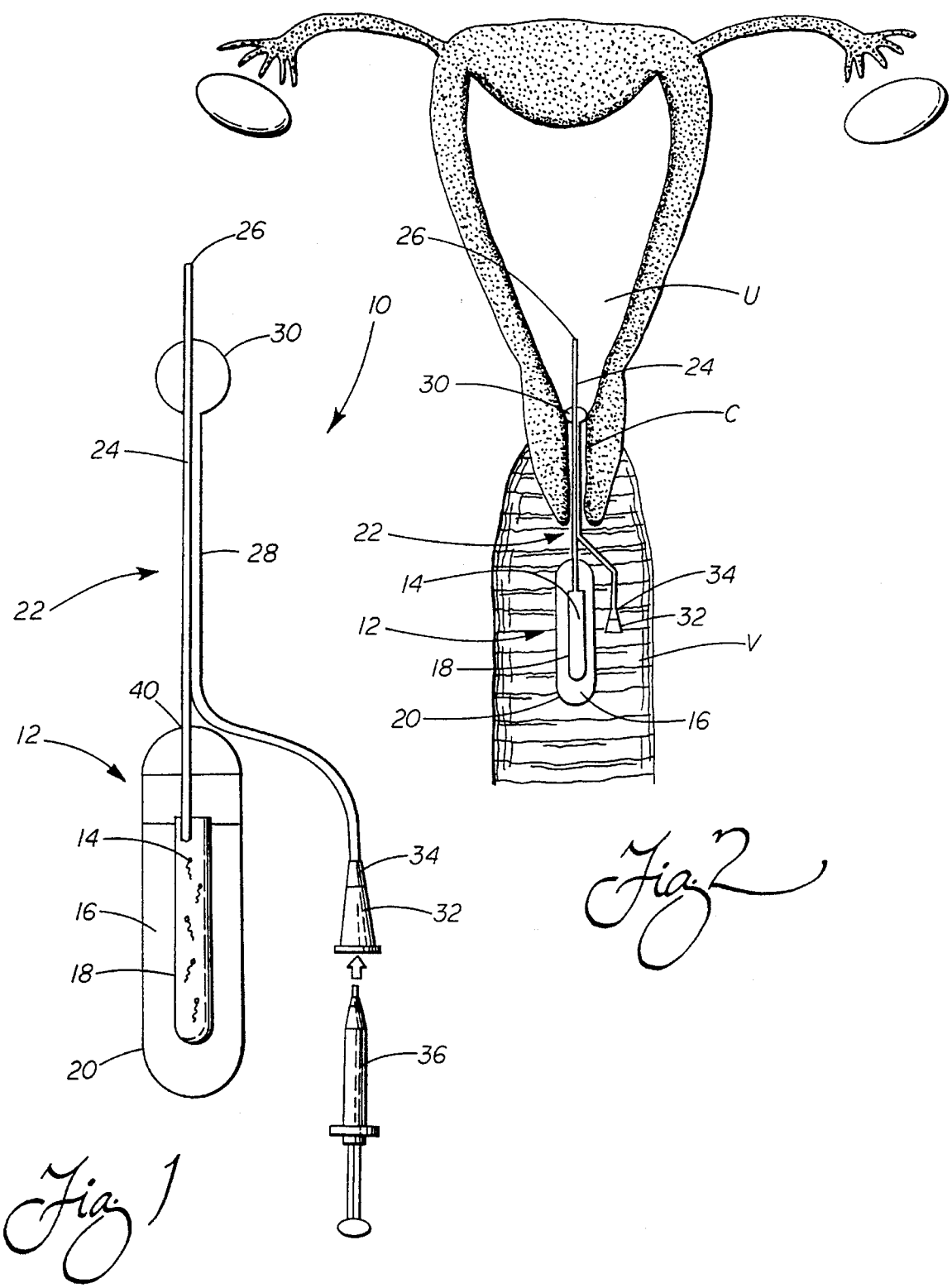
FIG. 1 is a schematical cross sectional view of the apparatus of the present invention for the time-released delivery of a selected preparation into the uterine cavity of a patient.
FIG. 2 is a schematical illustration showing the positioning of the apparatus of FIG. 1 in the body of a female patient.

Reference will now be made in detail to the present preferred embodiment of the invention, an example of which is illustrated in the accompanying drawing.

DETAILED DESCRIPTION OF THE INVENTION

Reference is now made to drawing FIG. 1 schematically showing the apparatus 10 of the present invention for the prolonged and gradual time-released delivery of a selected preparation into a patient's uterine cavity. Advantageously, as will become more apparent as the description hereof proceeds, the apparatus 10 may, for example, be utilized to treat infertility or various infectious diseases of the reproductive system of a female. Further, the apparatus 10 may be utilized not only to treat humans but also various animals and, particularly, domesticated mammalian farm animals.

As best shown in FIG. 1, the apparatus 10 includes an osmotic pump, generally designated by reference numeral 12. The osmotic pump 12 may be of a type known in the art such as the ALZET osmotic pump, Model 2001D, manufactured by ALZA Corporation. Such an osmotic pump 12 includes an inner reservoir chamber 14 for holding a predetermined amount of the selected preparation that is to be the subject of time-released delivery and an outer chamber 16 for holding an osmotically active agent. As shown, the inner and outer chambers 14, 16 are separated by an impermeable membrane 18. Of course, it should be appreciated that the impermeable membrane 18 must be nonreactive with the preparation to be administered utilizing the apparatus 10. Accordingly, for example, where the preparation is a sperm cell suspension for treating infertility, the impermeable membrane 18 must be constructed from a nonspermicidal material such as a silastic polymer.

The osmotic pump 12 also includes an outer, semi-permeable membrane 20 that separates the outer chamber 16 from the external environment. As will be described in greater detail below this semi-permeable membrane 20 allows the passage of water across the membrane into an osmotically active agent held in the outer chamber 16 so as to produce the necessary pressure on the inner reservoir chamber 14 to expel the selected preparation slowly over time.

As further shown in FIG. 1, the apparatus 10 also includes a double lumen catheter, generally designated by reference numeral 22. As with the impermeable membrane 18 of the osmotic pump 12, the catheter 22 must be constructed from a nonreactive material such as polyethylene. Such a material is also unlikely to produce any appreciable adverse immunological reaction in the patient.

As should be appreciated from reviewing FIG. 1 in detail, the first lumen 24 of the catheter 22 includes a proximal end in fluid communication with the inner reservoir chamber 14 of osmotic pump 12. Accordingly, the first lumen 24 receives the selected preparation expelled by the osmotic pump 12. The distal end or tip 26 of the first lumen 24 functions to deliver the expelled preparation into the uterine cavity of a patient in a manner described in greater detail below.

The second lumen 28 is operatively connected to the means for retaining the apparatus 10 in position in the patient. This means comprises an inflatable balloon 30 in fluid communication with the first end of the second lumen 28 adjacent to the tip 26 of the first lumen 24 and a syringe coupling 32 operatively connected in fluid communication with a second end of the second lumen 28. The syringe coupling 32 includes a check valve 34 of well known construction. By connecting a standard syringe 36 to the coupling 32, it is possible to inject air through the check valve 34 and the second lumen 28 into the balloon 30 so as to cause inflation thereof. When the syringe 36 is removed, the check valve 34 prevents the escape of air and maintains the inflation of the balloon 30.

As previously mentioned, the apparatus 10 of the present invention may be used to treat infertility of a patient by providing the prolonged time-released delivery of a sperm cell suspension to the uterine cavity of the patient. Alternatively, the apparatus 10 may be utilized in the prolonged time-released delivery of antibiotic drugs such as penicillins, erythromycins, cephalosporins and metronidazole to treat various reproductive system infections such as endometritis, pelvic inflammatory disease, endomyometritis and cervicitis. For purposes of illustration, the treatment of a patient for infertility will now be described in detail. It should be appreciated, however, that the apparatus 10 is not limited to use for this particular purpose.

A sperm cell suspension is prepared in a manner known in the art in a medium containing streptomycin and penicillin. More specifically, approximately 200 microliters of sperm cell suspension is introduced into the inner reservoir chamber 14 through port 40 of the osmotic pump 12 using a 1 cc syringe and tubing of the same size as the first lumen 24 portion of sperm delivery catheter 22. After filling the reservoir chamber 14, the filling tube is withdrawn from the port 40 and the distal end of the first lumen 24 of the catheter 22 is connected to the port so as to be in fluid communication with the inner reservoir chamber 14. The portion of the catheter 22 including the first lumen 24 and the port 40 of the osmotic pump 12 are secured together by frictional engagement or any other appropriate mechanism of fastening.

Next, is the positioning of the apparatus 10 into the patient. The patient is put in the supine position and the cervix is exposed with a bi-valve speculum or other appropriate medical device that has been sterilized for the procedure. The apparatus 10 is then inserted through the vagina V so that the tip 26 of the catheter 22 passes through the cervical canal C and is received in the uterine cavity U while the osmotic pump 12 is received in the vagina V (see FIG. 2). When in the proper position, the balloon 30, located about 1.5 cm from the tip 26 is also just above the cervical canal C in the uterine cavity U. The balloon 30 is inflated for the purpose of retaining the apparatus 10 in position and then the bi-valve speculum is carefully removed.

More specifically, the injection end of an air filled syringe 36 is inserted into the syringe coupling 32. Once seated, the plunger of the syringe 36 is depressed to direct the air from the syringe through the coupling 32 past the check valve 34 through the second lumen 28 of the catheter 22 into the balloon 30. Accordingly, the balloon 30 is inflated to a volume of approximately 1 cc. When so inflated, the apparatus 10 is prevented from pulling back through the cervical canal C and the tip 26 is, therefore, retained in the uterine cavity while the osmotic pump 12 at the other end of the first lumen 24 is retained in the vagina. As should be appreciated, the tip 26 extends outwardly from the inflated balloon 30 so as to insure that the balloon does not block the exit of the first lumen 24 through which the sperm cell suspension is delivered.

With the apparatus 10 now positively retained in position, the syringe 36 is removed. Of course, as indicated above, the check valve 34 prevents the escape of air and, therefore, the balloon 30 remains inflated. The patient is then allowed to carry on with her daily routine. Because the apparatus 10 is relatively small, the osmotic pump 12 being of only approximately 2 cm×1 cm and the double lumen catheter being only approximately 6 cm long with each lumen being approximately 0.25 cm in diameter, relatively little discomfort is experienced.

Immediately upon positioning, however, the apparatus 10 begins to function. Specifically, water from vaginal secretions passes through the semi-permeable membrane 20 and enters the outer chamber 16 that holds the osmotically active agent causing that agent to swell. Since the semi-permeable membrane 20 resists stretching and expansion, the entering water and resulting swelling increases the pressure in the outer chamber 16 pressing upon the impermeable membrane 18 of the inner reservoir chamber 14. As the pressure slowly builds, the impermeable membrane 18 compresses the inner reservoir chamber 14 thereby slowly expelling sperm cell suspension from the chamber into and through the first lumen 24 from which it is discharged from the tip 26 into the uterine cavity. The rate of pump discharge or preparation administration may be varied depending upon the desired result to be achieved. For intrauterine insemination a rate of approximately 8 microliters per hour may be provided. Accordingly, a sperm cell suspension of 200 microliters may be delivered to the uterine cavity during a period of 24 to 25 hours. This prolonged or extended period of administration or delivery of sperm cells into the uterine cavity more closely imitates the natural movement of sperm taking place following intercourse. As a result of closely mimicking this natural phenomenon, conception may be more readily induced than by other means known in the art to achieve intrauterine insemination.

Of course, once the treatment period is over and the apparatus 10 has discharged all of the sperm cell suspension by operation of the osmotic pump 12, the balloon 30 may be deflated and the apparatus 10 removed. This may be done by inserting a syringe 36 with plunger fully depressed into the syringe coupling 32 so as to engage and open the check valve 34. The plunger of the syringe is then withdrawn to draw air from balloon 30 and complete deflation. The deflated balloon 30 and catheter 22 may then easily pass through the cervical canal C so as to allow the entire apparatus 10 to be pulled from the vagina V and discarded.

As should be appreciated from the above description, the treatment of many infectious diseases of the reproductive system of a patient is also readily possible. More specifically, it is simply necessary to substitute an antibiotic preparation for the sperm cell suspension. That antibiotic preparation is then slowly delivered over an extended period of time to provide gradual and continuous treatment of the disease. As a result, treatment effectiveness is enhanced to the benefit of the patient.

In summary, numerous benefits results from employing the concepts of the present invention. The apparatus 10 provides for the reliable time-released delivery of a selected preparation into a patient's uterine cavity. Advantageously, the prolonged delivery or treatment may be of a duration of up to 24 hours or more. Thus, the apparatus 10 may be effectively utilized to treat a number of medical maladies from infertility to various infections of the female reproductive system. As a further advantage, the apparatus 10 is characterized by a relatively simple and inexpensive construction and is of a small size so as to minimize any discomfort associated with the treatment. Additionally, the patient may effectively continue with substantially all physical activities of a daily routine throughout the entire extended treatment period.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

I claim:

1. An apparatus for the time-released delivery of a selected preparation into a patient's uterine cavity, comprising:

an osmotic pump for expelling a selected preparation over time;

a catheter having a proximal end in fluid communication with said osmotic pump for receiving the selected preparation expelled by said osmotic pump and a distal end for delivering said expelled, selected preparation into the uterine cavity of the patient; and means for retaining said apparatus in position in the patient with said osmotic pump in the patient's vagina and said distal end of said catheter in the patient's uterine cavity.

2. The apparatus set forth in claim 1, wherein said retaining means is an inflatable balloon.

3. The apparatus set forth in claim 1, wherein said osmotic pump includes an inner reservoir chamber for holding a predetermined amount of the selected preparation, an outer chamber for holding an osmotically active agent, an impermeable membrane separating said inner and outer chambers and a semipermeable membrane separating said outer chamber from an external environment in which said osmotic pump rests.

4. An apparatus for the time-released delivery of a selected preparation into a patient's uterine cavity, comprising:

an osmotic pump for expelling the selected preparation over time;

a double lumen catheter including a first lumen having a proximal end in fluid communication with said osmotic pump for receiving the selected preparation expelled by said osmotic pump and a distal end for delivering said expelled, selected preparation into the uterine cavity of the patient; and means for retaining said apparatus in position in the patient with said osmotic pump in the patient's vagina and said distal end of said catheter in the patient's uterine cavity.

5. The apparatus set forth in claim 4, wherein said double lumen catheter includes a second lumen and said retaining means includes an inflatable balloon and a means for selectively inflating said balloon, said inflatable balloon being in fluid communication with a first end of said second lumen adjacent said distal end of said first lumen and said inflating means includes a coupling operatively connected to a second end of said second lumen.

6. The apparatus set forth in claim 5, wherein said coupling includes a check valve to prevent air from escaping from said balloon after inflation.

7. The apparatus set forth in claim 6, wherein said inflating means further includes a syringe that is connected to said coupling in order to deliver air to said inflatable balloon.

8. The apparatus set forth in claim 7, wherein said osmotic pump includes an inner reservoir chamber for holding a predetermined amount of the selected preparation, an outer chamber for holding an osmotically active agent, an impermeable membrane separating said inner and outer chambers and a semipermeable membrane separating said outer chamber from an external environment in which said osmotic pump rests.

9. The apparatus set forth in claim 5, wherein said osmotic pump includes an inner reservoir chamber for holding a predetermined amount of the selected preparation, an outer chamber for holding an osmotically active agent, an impermeable membrane separating said inner and outer chambers and a semipermeable membrane separating said outer chamber from an external environment in which said osmotic pump rests.

10. The apparatus set forth in claim 4, wherein said osmotic pump includes an inner reservoir chamber for holding a predetermined amount of the selected preparation, an outer chamber for holding an osmotically active agent, an impermeable membrane separating said inner and outer chambers and a semipermeable membrane separating said outer chamber from an external environment in which said osmotic pump rests.

11. A method of providing time-released delivery of a selected preparation into a patient's uterine cavity by means of an apparatus including an osmotic pump operatively connected to a catheter having a lumen for delivering the selected preparation, comprising:

charging the osmotic pump with the selected preparation;

positioning the apparatus so that the osmotic pump is in the patient's vagina and the catheter extends through the patient's cervical canal into the patient's uterine cavity thereby providing fluid communication between the osmotic pump and uterine cavity; and positively retaining the apparatus in position.

12. The method set forth in claim 11, wherein said retaining step includes:

providing an inflatable balloon on the catheter; and inflating the balloon after positioning in the patient's uterine cavity.

13. A method of providing time released delivery of spermatozoa into a patient's uterine cavity for purposes of artificial insemination by means of an apparatus including an osmotic pump operatively connected to a catheter having a lumen for delivering the spermatozoa, comprising charging the osmotic pump with the spermatozoa;

positioning the apparatus so that the osmotic pump is in the patient's vagina and the catheter extends through the patient's cervical canal into the patient's uterine cavity thereby providing fluid communication between the osmotic pump and uterine cavity; and positively retaining the apparatus in position.

14. The method set forth in claim 13, wherein said retaining step includes:

providing an inflatable balloon on the catheter; and inflating the balloon after positioning in the patient's uterine cavity.

* * * * *

UNITED STATES PATENT AND TRADEMARK OFFICE
CERTIFICATE OF CORRECTION

PATENT NO. : 5,562,654
DATED : October 8, 1996
INVENTOR(S) : Todd T. Smith

It is certified that error appears in the above-indentified patent and that said Letters Patent is hereby corrected as shown below:

In Claim 1, column 7, line 41, following the word "having", insert --a lumen with--.

Signed and Sealed this

Seventeenth Day of December, 1996

Attest:

BRUCE LEHMAN

Attesting Officer    Commissioner of Patents and Trademarks